United States Patent [19]
Medich et al.

[11] Patent Number: 5,276,155
[45] Date of Patent: Jan. 4, 1994

[54] PROCESS FOR THE RESOLUTION OF (±)-α[2-[ACETYL](1-METHYLETHYL)AMINOIETHYL]-α-(2-CHLOROPHENY)-1-PIPERIDINEBUTANAMIDE

[75] Inventors: John R. Medich, Des Plaines; Gatis Plume, Buffalo Grove, both of Ill.

[73] Assignee: G. D. Searle & Co., Chicago, Ill.

[21] Appl. No.: 811,182

[22] Filed: Dec. 20, 1991

[51] Int. Cl.$^5$ .................. C07D 207/04; C07D 295/18
[52] U.S. Cl. .................................................. 546/233
[58] Field of Search .............................. 546/229, 233

[56] References Cited

U.S. PATENT DOCUMENTS

| | | |
|---|---|---|
| 4,639,524 | 1/1987 | Desai et al. ............ 546/233 |
| 5,097,035 | 3/1992 | Desai et al. ............ 546/226 |

FOREIGN PATENT DOCUMENTS

0170901A1 2/1986 European Pat. Off. ............ 546/229

OTHER PUBLICATIONS

Ingersoll, *J. Am. Chem. Soc.*, (47), 1168–1173, 1925.
Ingersoll, *J. Am. Chem. Soc.* 50, 2264–2267 1928.

*Primary Examiner*—C. Warren Ivy
*Assistant Examiner*—Zinna N. Davis
*Attorney, Agent, or Firm*—Joy Ann Serauskas; Roger A. Williams

[57] ABSTRACT

A process for the resolution of (±)-α-[2-[acetyl(1-methylethyl)amino]ethyl-α-(2-chlorophenyl)-1-piperidinebutanamide having the following structure

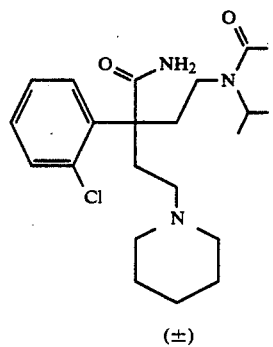

(±)

into its (+) and (−) enantiomers using camphorsulfonic acid.

3 Claims, No Drawings

PROCESS FOR THE RESOLUTION OF (±)-α[2-[ACETYL](1-METHYLETHYL) AMINOIETHYL]-α-(2-CHLOROPHENY)-1-PIPERIDINEBUTANAMIDE (±)-α-[2-[Acetyl(1-methylethyl)amino]ethyl]-α-(2-chlorophenyl)-1-piperidinebutanamide which is a racemic mixture is useful by virtue of its ability to inhibit ventricular arrhythmia. A complete discussion of (±)α-[2-[acetyl(1-methylethyl)amino]ethyl]-α-(2-chlorophenyl)-1-piperidinebutanamide usefulness as an antiarrhythmic agent is given in U.S. Pat. No. 4,639,524. Given its potential usefulness as a pharmacological agent, it became desirable to develop a convenient and cost effective process for its resolution.

BACKGROUND OF THE INVENTION

Ingersoll, *J. Am. Chem. Soc.* (47), 1168–1173 (1925) discusses a method for the resolution of externally compensated acids and bases by which both active forms are obtained completely pure. This method utilizes stereospecific camphorsulfonic acid.

Ingersoll, *J. Am. Chem. Soc.* (50), 2264–2267 (1928) discusses the resolution of inactive iso-diphenylhydroxy-ethylamine with d and dl-camphor sulfonic acids.

SUMMARY OF THE INVENTION

The present invention provides a convenient and cost effective manufacturing process for the resolution of (+)-α-[2-[acetyl(1-methylethyl)amino]ethyl]-α-(2-chlorophenyl)-1-piperidinebutanamide into its two enantiomers

[±]-α-[2-[acetyl(1-methylethyl)
amino]ethyl]-α-(2-chlorophenyl)-1-
piperidinebutanamide which is represented by the following structural formula

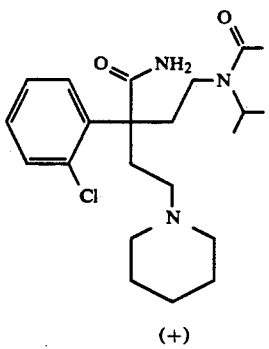

(+)

and

[−]-α-[2-[acetyl(1-methylethyl)
aminoethyl]-α-(2-chlorophenyl)-1-
piperidinebutanamide which is represented by the following structural formula

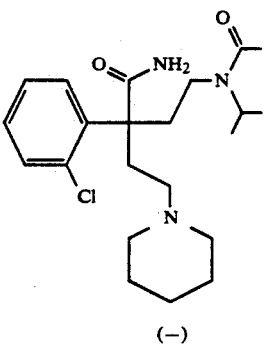

(−)

Both enantiomers show electrophysiologic effects in both the upper and lower parts of the heart. This electrophysiological activity would indicate that the enantiomers would be useful as antiarrhythmic agents.

The convenience of the process is demonstrated by the synthetic route comprising only two steps. The cost effectiveness of the process is demonstrated by the final product being produced in high yield and high quality.

The process of this invention is illustrated by the following Scheme I.

Scheme I

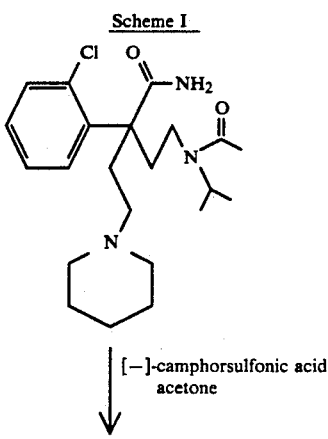

↓ [−]-camphorsulfonic acid
acetone

-continued
Scheme I
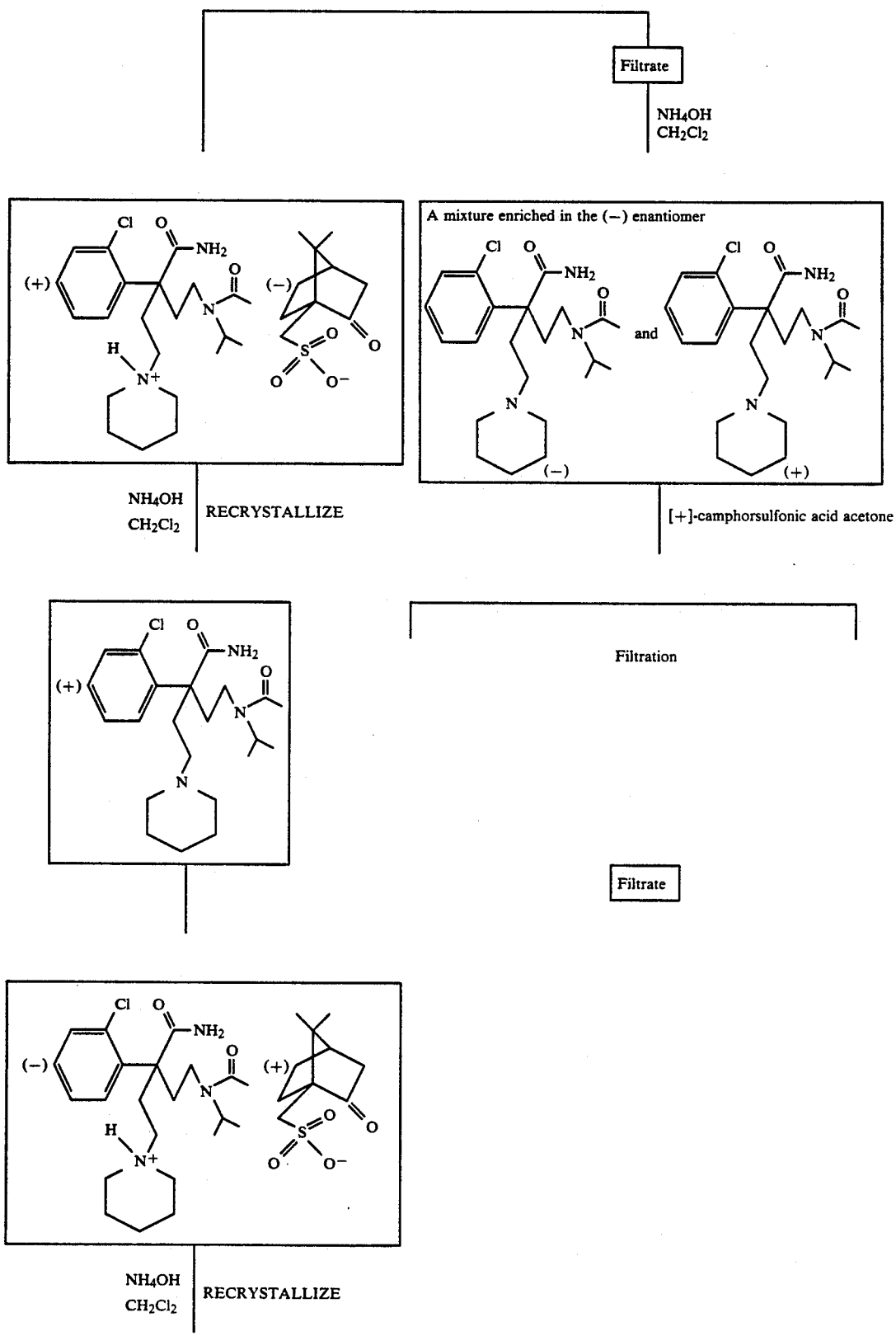

-continued
Scheme I

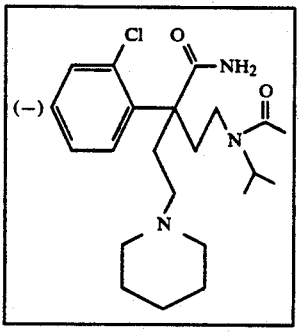

In the practice of this invention which is illustrated in Scheme I, [±]-α-[2-[acetyl(1-methylethyl)amino]ethyl]-α-(2-chlorophenyl)-1-piperidinebutanamide is mixed in an organic solvent and (1R)-(−)-10 camphorsulfonic acid is added to the solution. The solid [+]-α-[2-[acetyl(1-methylethyl)amino]ethyl]-α-(2-chlorophenyl)-1-piperidinebutanamide(−)camphorsulfonic salt is obtained by filtration. In a preferred embodiment of the invention the stereospecific camphorsulfonic acid is added to a mixture of acetone and [±]-α-[2-[acetyl(1-methylethyl)amino]ethyl]-α-(2-chlorophenyl)-1-piperidinebutanamide and the resulting solution is stirred. Seeding of the solution with [+]-α-[2-[acetyl(1-methylethyl)amino]ethyl]-α-(2-chlorophenyl)-1-piperidinebutanamide(−)camphorsulfonic acid salt initiates the crystallization of [+]-α-[2-[acetyl(1-methylethyl)amino]ethyl]-α-(2-chlorophenyl)-1-piperidinebutanamide(−)camphorsulfonic salt. The solvent is removed by filtrating. The crystalline product is washed with acetone, pulled dry under N₂ and dried in a vacuum oven at 50° C. While acetone is a preferred solvent, other solvents such as ethyl acetate and methylethyl ketone could be used in the practice of this invention.

The diastereomeric salt is converted to [+]-α-[2-[acetyl(1-methylethyl)amino]ethyl]-α-(2-chlorophenyl)-1-piperidinebutanamide by treatment with a base. In a preferred embodiment of the invention the free base formation is conducted at room temperature for fifteen minutes. The diastereomeric salt is dissolved in water and methylene chloride. The reaction mixture is stirred and then treated with ammonium hydroxide. The organic layer is washed with water, dried and filtered. Removal of the solvent gives [+]-α-[2-[acetyl(1-methylethyl)amino]ethyl]-α-(2-chlorophenyl)-1-piperidinebutanamide as a crystalline product. While ammonium hydroxide is a preferred base, other bases such as sodium hydroxide, potassium hydroxide, sodium carbonate or potassium carbonate could be used.

The filtrate from the preceding filtration step is concentrated to give a solid which is treated with base as described above to provide a mixture of [+]-α-[2-[acetyl(1-methylethyl)amino]ethyl]-α-(2-chlorophenyl)-1-piperidinebutanamide and [−]-α-[2-[acetyl(1-methylethyl)aminoethyl]-α-(2-chlorophenyl)-1-piperidinebutanamide. This mixture is enriched in the (−) enantiomer. It is essential in the practice of this invention that the percentage of the (−) enantiomer in the enriched mixture not be below 70% with 80% or above being preferred. This mixture is mixed with (+)-camphorsulfonic acid in acetone. After seeding with [−]-α-[2-[acetyl(1-methylethyl) aminoethyl]-α-(2-chlorophenyl)-1-piperidinebutanamide (+)-camphorsulfonic acid salt and crystallization the [−]-α-[2-[acetyl(1-methylethyl)aminoethyl]-α-(2-chlorophenyl)-1-piperidinebutanamide (+)-camphorsulfonic acid salt is isolated by filtration. This salt is treated with base in the manner described above to provide [−]-α-[2-[acetyl(1-methylethyl)aminoethyl]-α-(2-chlorophenyl)-1-piperidinebutanamide.

The stereospecific camphorsulfonic acid, namely the (1R)-(−)-10 camphorsulfonic acid or (1S)-(+)-10-camphorsulfonic acid is commercially available.

The following examples are intended to further illustrate the present invention and not to limit the invention in spirit or scope. In the examples, all parts are parts by weight and temperature is in degrees Celsius unless otherwise expressly set forth.

EXAMPLE 1

Preparation of
(+)-α-[2-[acetyl(1-methylethyl) amino]ethyl]-α-(2-chlorophenyl)-1-piperidinebutanamide

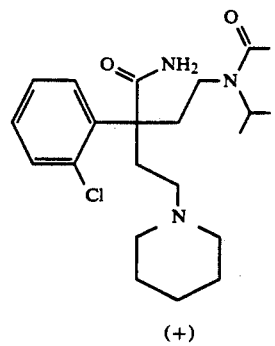

(+)

Step A 730 g of [±]-α-[2-[acetyl(1-methylethyl)amino]ethyl]-α-(2-chlorophenyl)-1-piperidinebutanamide was mixed with 5.5 mL of acetone in a flask equipped with a mechanical stirrer. To the stirred mixture was added 416 g of (1R)-(−)-10-camphor sulfonic acid and an additional 500 ml of acetone. Addition caused the temperature of the solution to rise to 50° C. The stirred solution was now seeded with 100 mg of (+)-α-[2-[acetyl(1-methylethyl)amino]ethyl]-α-(2-chlorophenyl)-1-piperidinebutanamide (−)-camphorsulfonic acid salt and stirring was continued overnight.

The resulting fine particle crystalline product was filtered, washed with acetone, and pulled dry under $N_2$. The filtrate containing an enriched mixture of [−]-α-[2-[acetyl(1-methylethyl)aminoethyl]-α-(2-chlorophenyl)-1-piperidinebutanamide(−)camphorsulphonic acid salt is used in Example 2.

Drying of the product in a vacuum oven at 50° C. overnight gave 437 g of the salt. The salt had the following elemental analysis:

Required for $C_{32}H_{50}ClN_3O_6S$: C, 60.03; H, 7.87; N, 6.56;

Cl, 5.54; S, 5.01,

Found: C, 60.06; H, 7.93; N, 6.59; Cl, 5.28; S, 5.14 m.p. 191.5°–193° C.

Step B

The product of Step A (436 g) was dissolved in 1500 ml of water. To this solution was added 2000 ml of methylene chloride and 92 ml of 29.4% ammonium hydroxide solution. The solution was now stirred for 15 minutes. The organic layer was separated, washed (2×) with 1 L of water, dried over anhydrous $K_2CO_3$ and filtered. Stripping of the solvent under vacuum yielded 294 g of the crude product. The crude product was dissolved in 2 L of refluxing ethyl acetate and filtered while hot. The filtrate was transferred to a flask equipped with a magnetic stirring bar and stirred. Seeding of the filtrates with [+]-α-[2-[acetyl(1-methylethyl)amino]ethyl]-α-(2-chlorophenyl)-1-piperidinebutanamide caused the product to crystallize as a thick slurry. Stirring was discontinued and the slurry was allowed to stand overnight. The slurry was broken up, filtered and washed with 200 ml of ethyl acetate. The product was pulled dry and then dried in a vacuum at 50° C. This procedure gave 239 g of the title product. Concentration of the filtrates gave additional [+]-α-[2-[acetyl(1-methylethyl)amino]ethyl]-α-(2-chlorophenyl)-1-piperidinebutanamide for an overall yield of 70%.

The title product had the following elemental analysis:

Required for $C_{22}H_{34}ClN_3O_2$: C, 64.77; H, 8.40; N, 10.30;

Cl, 8.69,

Found: C, 64.73; H, 8.58; N, 10.20; Cl, 8.76.

Specific Rotation: $[\alpha]_D^{25} = +4.9°$ (C=1 in $CHCl_3$).

EXAMPLE 2

Preparation of (−)-α-[2-[acetyl(1-methylethyl) amino]ethyl]-α-(2-chlorophenyl)-1-piperidinebutanamide

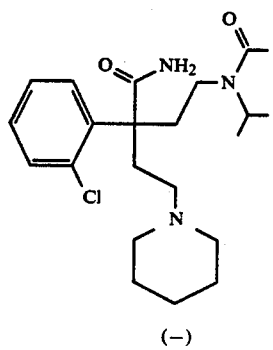

(−)

Step A

The filtrate from example 1 containing an enriched sample of [−]-α-[2-[acetyl(1-methylethyl)amino]ethyl]-α-(2-chlorophenyl)-1-piperidinebutanamide(−)-camphorsulphonic acid salt was concentrated to a solid weighing 613 g. The material was taken up in 1500 ml of water then made basic with ammonium hydroxide (100 ml). The mixture was extracted with two 700 ml portions of methylene chloride. The organic layers were dried over $K_2CO_3$ and filtered. The filtrate was concentrated to provide 417 g of an enriched sample of (−)-α-[2-[acetyl(1-methylethyl)amino]ethyl]-α-(2-chlorophenyl)-1-piperidinebutanamide. To this product in 2.0 L of acetone with stirring is added (+)-camphorsulfonic acid (207 g). The solution is seeded with (−)-α-[2-[acetyl(1-methylethyl)amino]ethyl]-α-(2-chlorophenyl)-1-piperidinebutanamide(+)-camphorsulfonic acid and an additional 500 ml of acetone is added. Stirring was continued overnight. The resulting fine particle crystalline product was filtered, washed with acetone, and pulled dry under $N_2$. Drying of the product in a vacuum oven at 50° C. overnight gave 404 g of the salt.

m.p. 190°–193° C.

Step B

The product of Step A (404 g) was dissolved in 1200 ml of water. To this solution was added 1400 ml of methylene chloride and 120 ml of 29.4% ammonium hydroxide solution. The solution was now stirred for 15 minutes. The organic layer was separated, washed (2×) with 1 L of water, dried over anhydrous $K_2CO_3$ and filtered. Stripping of the solvent under vacuum yielded 335 g of the crude product. The crude product was dissolved in 2 L of refluxing ethyl acetate and filtered hot. The filtrates were transferred to a flask equipped with a magnetic stirring bar and stirred. Seeding of the filtrates with [−]-α-[2-[acetyl(1-methylethyl)amino]ethyl]-α-(2-chlorophenyl)-1-piperidinebutanamide caused the product to crystallize as a thick slurry. Stirring was discontinued and the slurry was allowed to stand overnight. The slurry was broken up, filtered and washed with 200 ml of ethyl acetate. The product was pulled dry and then dried in a vacuum over at 50° C. This procedure gave 255 g of the title product. The title product had the following elemental analysis:

Required for $C_{22}H_{34}ClN_3O_2$: C, 64.77; H, 8.40; N, 10.30;

Cl, 8.69,

Found: C, 64.73; H, 8.58; N, 10.20; Cl, 8.76.

Specific Rotation: $[\alpha]_D^{25} = -5.4°$ (C=1 in $CHCl_3$).

What we claim is:

1. A process for the resolution of [±]-α-[2-[acetyl(1-methylethyl)amino]ethyl]-α-(2-chlorophenyl)-1-piperidinebutanamide which has the following structural formula

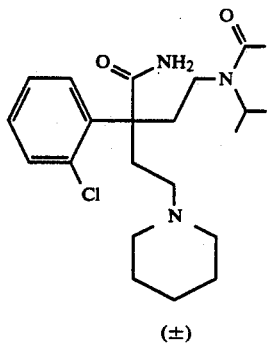

(±)

into [+]-α-[2-[acetyl(1-methylethyl)amino]ethyl]-α-(2-chlorophenyl)-1-piperidinebutanamide which has the following structural formula

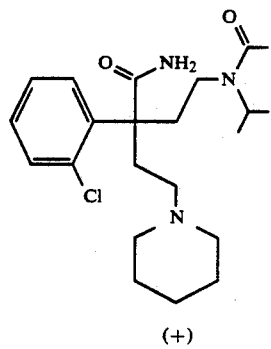

(+)

and [−]-α-[2-[acetyl(1-methylethyl)amino]ethyl]-α-(2-chlorophenyl)-1-piperidinebutanamide which has the following structural formula

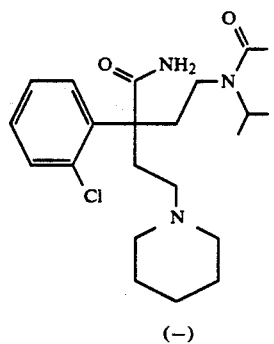

(−)

comprising the steps of a) treating [±]-α-[2-[acetyl(1-methylethyl)amino]ethyl]-α-(2-chlorophenyl)-1-piperidinebutanamide with (1R)-(−)-10-camphorsulfonic acid in the presence of a solvent to give a solution and seeding the resultant solution with [+]-α-[2-[acetyl(1-methylethyl)amino]ethyl]-α-(2-chlorophenyl)-1-piperidinebutanamide(−)camphorsulfonic acid salt to give by filtration [+]-α-[2-[acetyl(1-methylethyl) amino]ethyl]-α-(2-chlorophenyl)-1-piperidinebutanamide (−)-camphorsulfonic acid salt as a solid;

b) dissolving the solid [+]-α-[2-[acetyl(1-methylethyl)amino]ethyl]-α-(2-chlorophenyl)-1-piperidinebutanamide (−)-camphorsulfonic acid salt from step a) in water and solvent, treating the resultant solution with base, separating the organic layer from said solution and washing, drying, filtering and evaporating the separated organic layer to give as a solid (+)-α-[2-[acetyl(1-methyl)amino]ethyl]-α-(2-chlorophenyl)-1-piperidinebutanamide;

(c) concentrating the filtrations from step a) to give a solid, dissolving the solid in water and treating the resultant solution with base to give a mxiture of [⇌]-α-[2-[acetyl(1-methylethyl)amino]ethyl]-α-(2-chlorophenyl)-1-piperidinebutanamide and [−]-α-[2-[acetyl(1-methylethyl)aminoethyl]-α-(2-chlorophenyl)-1-piperidinebutanamide which is enriched in the [−]-α-[2-[acetyl(1-methylethyl)amino]ethyl]-α-(2-chlorophenyl)-1-piperidinebutanamide;

d) extracting the mixture from step c) with solvent, separating the resultant organic layer, washing, drying, filtering and evaporating the organic layer to give a solid which is enriched with [−]-α-[2-[acetyl(1-methylethyl)amino]ethyl]-α-(2-chlorophenyl)-1-piperidinebutanamide, treating said solid with (+)-camphorsulfonic acid in the presence of a solvent and seeding the resultant solution with [−]-α-[2-[acetyl(1-methyl)aminoethyl]-α-(2-chlorophenyl)-1-piperidinebutanamide (+)-camphorsulfonic acid salt to give by filtration [−]-α-[2-[acetyl(1-methylethyl)aminoethyl]-α-(2-chlorophenyl)-1-piperidinebutanamide(+)-camphorsulfonic acid salt as a solid; and e) treating [−]-α-[2-[acetyl(1-methylethyl) aminoethyl]-α-(2-chlorophenyl)-1-piperidinebutanamide (+)-camphorsulfonic acid salt from step d) with base to give [−]-α-[2-[acetyl(1-methylethyl) aminoethyl]-α-(2-chlorophenyl)-1-piperidinebutanamide.

2. The process according to claim 1 wherein the solvent is acetone.

3. The process according to claim 1 wherein the base is ammonium hydroxide.

* * * * *

UNITED STATES PATENT AND TRADEMARK OFFICE
CERTIFICATE OF CORRECTION

PATENT NO. : 5,276,155

DATED : January 4, 1994

INVENTOR(S) : Medich, et al.

It is certified that error appears in the above-identified patent and that said Letters Patent is hereby corrected as shown below:

On the cover page, the title reading "PROCESS FOR THE RESOLUTION OF (±)-α[2-[ACETYL](1-METHYLETHYL)AMINO1ETHYL]-α-(2-CHLOROPHENY)-1-PIPERIDINEBUTANAMIDE" should read -- PROCESS FOR THE RESOLUTION OF (±)-α[2-[ACETYL(1-METHYLETHYL)AMINO]ETHYL]-α-(2-CHLOROPHENYL)-1-PIPERIDINEBUTANAMIDE --.

Column 1, line 4, reading "PROCESS FOR THE RESOLUTION OF (±)-α[2-[ACETYL](1-METHYLETHYL)AMINO1ETHYL]-α-(2-CHLOROPHENY)-1-PIPERIDINEBUTANAMIDE" should read -- PROCESS FOR THE RESOLUTION OF (±)-α[2-[ACETYL(1-METHYLETHYL)AMINO]ETHYL]-α-(2-CHLOROPHENYL)-1-PIPERIDINEBUTANAMIDE --.

Column 1, line 31, reading "(+)" should read -- (±) --.

Column 10, line 19, reading "(1-methyl)" should read -- (1-methylethyl) --.

Column 10, line 23, reading "mixture of [₹] should read -- mixture of (+) --.

UNITED STATES PATENT AND TRADEMARK OFFICE
CERTIFICATE OF CORRECTION

PATENT NO.  : 5,276,155
DATED       : January 4, 1994
INVENTOR(S) : Medich, et al.

It is certified that error appears in the above-identified patent and that said Letters Patent is hereby corrected as shown below:

Column 10, line 38, reading "(1-methyl)" should read -- (1-methylethyl) --.

Signed and Sealed this

Eleventh Day of July, 1995

*Attest:*

BRUCE LEHMAN

*Attesting Officer*       *Commissioner of Patents and Trademarks*